(12) United States Patent
Hull

(10) Patent No.: US 7,062,386 B1
(45) Date of Patent: Jun. 13, 2006

(54) METHOD TO ESTIMATE THE MECHANICAL PROPERTIES OF A SOLID MATERIAL SUBJECTED TO ISONIFICATION

(75) Inventor: Andrew J. Hull, Newport, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 282 days.

(21) Appl. No.: 10/730,194

(22) Filed: Dec. 4, 2003

(51) Int. Cl.
*G01B 5/28* (2006.01)

(52) U.S. Cl. .......................... 702/39; 73/597

(58) Field of Classification Search ............... 702/39, 702/159, 171, 172, 1; 73/597, 579, 603, 73/624, 625
See application file for complete search history.

(56) References Cited

U.S. PATENT DOCUMENTS

| | | | |
|---|---|---|---|
| 4,061,017 A | 12/1977 | Sloane et al. | |
| 4,352,292 A | 10/1982 | Madigosky et al. | |
| 4,418,573 A | 12/1983 | Madigosky et al. | |
| 4,633,449 A | 12/1986 | Ingram | |
| 4,674,334 A | 6/1987 | Chimenti et al. | |
| 5,143,072 A | 9/1992 | Kantorovich et al. | |
| 5,363,701 A | 11/1994 | Lee et al. | |
| 5,365,457 A | 11/1994 | Madigosky | |
| 5,495,763 A | 3/1996 | Rhodes et al. | |
| 5,533,399 A | 7/1996 | Gibson et al. | |
| 5,621,172 A | 4/1997 | Wilson et al. | |
| 5,784,333 A * | 7/1998 | Tang et al. | 367/30 |
| 5,804,727 A * | 9/1998 | Lu et al. | 73/597 |
| 6,139,496 A | 10/2000 | Chen et al. | |
| 6,155,116 A | 12/2000 | Muench et al. | |
| 6,609,428 B1 | 8/2003 | Hull | |
| 2004/0054474 A1 * | 3/2004 | Zeroug et al. | 702/1 |

OTHER PUBLICATIONS

D.M.Norris, Jr. & Wun-Chung Young, Complex-Modulus Measurement by Longitudinal Vibration Testing, Journal; Feb. 1970, pp. 93-96, vol. 10, Experimental Mechanics, USA.

W.M. Madigosky & G.F. Lee, Improved Resonance Technique for Materials Characterization, Journal, Apr. 1983, pp. 1374-1377, vol. 73, No. 4.

(Continued)

*Primary Examiner*—John Barlow
*Assistant Examiner*—Xiuqin Sun
(74) *Attorney, Agent, or Firm*—Michael P. Stanley; James M. Kasischke; Jean-Paul A. Nasser

(57) ABSTRACT

A method for measuring the complex frequency-dependent dilatational and shear wavespeeds of a slab of material subjected to insonification. Transfer functions that are obtained by insonifying the material at different angles. Once this is accomplished, the transfer functions are manipulated with an inverse method to yield closed form values of dilatational and shear wavespeeds at any test frequency. The wavespeeds can be combined to determine complex Lamé constants, complex Young's modulus, complex shear modulus, and complex Poisson's ratio.

3 Claims, 15 Drawing Sheets

OTHER PUBLICATIONS

S.L. Garrett, Resonant Acoustic Determination of Elastic Moduli, Journal, Jul. 1990, pp. 21-220, vol. 88, No. 1, Journal of the Acoustical Society of America, USA.

B.J. Dobson, A Straight Time Technique for Extracting Modal Properties from Frequency Response Data, Journal, 1987, pp. 29-40, vol. 1.

T. Pritz, Transfer Function Method for Investigating the Complex Modulus of Acoustic Materials: Rod-Like Specimen, Journal, 1982, pp. 359-376, vol. 81.

T. Pritz, Frequency Dependencies of Complex Moduli and Complex Poisson's Ratio or Real Solid Materials, Journal, 1998, pp. 83-104, vol. 214.

* cited by examiner

US 7,062,386 B1

METHOD TO ESTIMATE THE MECHANICAL PROPERTIES OF A SOLID MATERIAL SUBJECTED TO ISONIFICATION

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to a method for measuring mechanical characteristics of materials. More particularly, this invention provides a method which uses transfer functions obtained by insonifying the material at different angles. Once obtained, the transfer functions are manipulated to yield closed form values of dilatational and shear wavespeeds. The wavespeeds are combined to determine complex Lamé constants, complex Young's modulus, complex shear modulus, and complex Poisson's ratio for the material.

(2) Description of the Prior Art

Measuring the mechanical properties of slab-shaped (i.e., plates) materials are important in that these parameters significantly contribute to the static and dynamic response of structures built with such materials. Resonant techniques have been used to identify and measure longitudinal properties for many years (See D. M. Norris, Jr., and W. C. Young, "Complex Modulus Measurements by Longitudinal Vibration Testing," *Experimental Mechanics*, Volume 10, 1970, pp. 93–96; W. M. Madigosky and G. F. Lee, "Improved Resonance Technique for Materials Characterization," *Journal of the Acoustical Society of America*, Volume 73, Number 4, 1983, pp. 1374–1377; S. L. Garrett, "Resonant Acoustic Determination of Elastic Moduli," *Journal of the Acoustical Society of America*, Volume 88, Number 1, 1990, pp. 210–220; G. F. Lee and B. Hartmann, U.S. Pat. No. 5,363,701; G. W. Rhodes, A. Migliori, and R. D. Dixon, U.S. Pat. No. 5,495,763; and R. F. Gibson and E. O. Ayorinde, U.S. Pat. No. 5,533,399).

These methods are based on comparing the measured eigenvalues of a structure to predicted eigenvalues from a model of the same structure. The model of the structure must have well-defined (typically closed form) eigenvalues for these methods to work. Additionally, resonant techniques only allow measurements at resonant frequencies. Most of these methods typically do not measure shear wavespeeds (or modulus) and do not have the ability to estimate Poisson's ratio.

Comparison of analytical models to measured frequency response functions is another method used to estimate stiffness and loss parameters of a structure (See B. J. Dobson, "A Straight-Line Technique for Extracting Modal Properties From Frequency Response Data," *Mechanical Systems and Signal Processing*, Volume 1, 1987, pp. 29–40; T. Pritz, "Transfer Function Method for Investigating the Complex Modulus of Acoustic Materials: Rod-Like Specimen," *Journal of Sound and Vibration*, Volume 81, 1982, pp. 359–376; W. M. Madigosky and G. F. Lee, U.S. Pat. No. 4,352,292; and W. M. Madigosky and G. F. Lee, U.S. Pat. No. 4,418,573). When the analytical model agrees with one or more frequency response functions, the parameters used to calculate the analytical model are considered accurate. If the analytical model is formulated using a numerical method, a comparison of the model to the data can be difficult due to dispersion properties of the materials.

Another method to measure stiffness and loss is to deform the material and measure the resistance to the indentation (See W. M. Madigosky, U.S. Pat. No. 5,365,457). However, this method can physically damage the specimen if the deformation causes the sample to enter the plastic region of deformation.

Others methods have used insonification as a means to determine defects in composite laminate materials (See D. E. Chimenti and Y. Bar-Cohen, U.S. Pat. No. 4,674,334). However, these methods do not measure material properties.

A method does exist to measure shear wave velocity and Poisson's ratio in the earth using boreholes and seismic receivers (See J. D. Ingram and O. Y. Liu, U.S. Pat. No. 4,633,449). However, this method needs a large volume of material and is not applicable to slab-shaped samples. Additionally, it needs a borehole in the volume at some location.

In view of the above, there is a need for a method to measure complex frequency-dependent dilatational and shear wavespeeds of materials subject to insonification. Once the wavespeeds are identified, the complex frequency-dependent Young's and shear moduli and complex frequency-dependent Poisson's ratio can also be measured (or estimated).

SUMMARY OF THE INVENTION

Accordingly, it is a general purpose and primary object of the present invention to provide a method to measure (or estimate) the complex frequency-dependent dilatational and shear wavespeeds of a slab of material subjected to insonification.

It is a further object of the present invention to provide a method to measure (or estimate) the shear modulus of a slab of material subjected to insonification.

It is a still further object of the present invention to provide a method to measure (or estimate) the Young's modulus of a slab of material subjected to insonification.

It is a still further object of the present invention to provide a method to measure (or estimate) the complex frequency-dependent Poisson's ratio of a slab of material subjected to insonification.

To attain the objects described, there is provided a method which uses three transfer functions that are obtained by insonifying the material at different angles. Once this is accomplished, the transfer functions are manipulated with an inverse method to yield closed form values of dilatational and shear wavespeeds at any given test frequency. The wavespeeds are combined to determine complex Lamé constants, complex Young's modulus, complex shear modulus, and complex Poisson's ratio.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
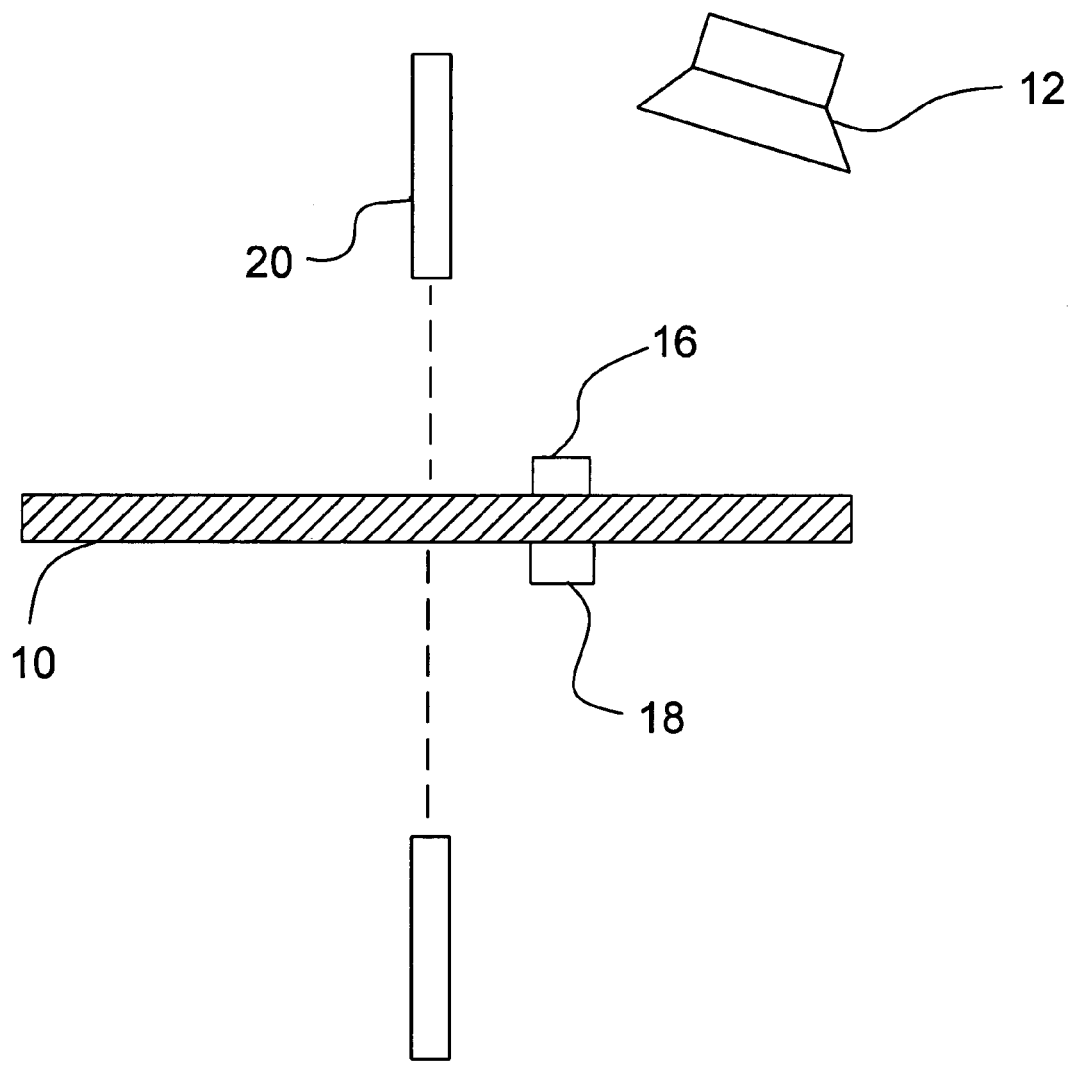
FIG. 1 depicts a test setup to insonify and gather measurements for a specimen of material.

Referring now to the drawings wherein like numerals refer to like elements throughout the several views, one sees that FIG. 1 depicts the isonification of a slab-shaped test specimen 10 by a speaker (or projector) 12. Insonification consists of loading the specimen 10 on one entire side with an acoustic wave originating at the speaker 12. The speaker 12 is located at a sufficient distance from the specimen 10 that the acoustic wave is nearly a plane wave by the time it contacts the specimen. The insonification is usually done at multiple frequencies and multiple angles.

For the method presented, a frequency sweep (swept sine) is conducted at three different insonification angles. The transfer function data is collected with either accelerometers 16, 18 on both sides which record accelerations, or laser velocimeters 20, 22 shining on both sides which record velocities. In the swept sine mode, the transfer functions of acceleration divided by acceleration or velocity divided by velocity are both equal to displacement divided by displacement. The time domain data are Fourier transformed into the frequency domain and then recorded as complex transfer functions, typically using a spectrum analyzer (not shown).

The motion of the specimen 10 is governed by the equation $$\mu \nabla^2 u + (\lambda + \mu) \nabla \circ u = \rho \frac{\partial^2 u}{\partial t^2}, \tag{1}$$

where $\lambda$ and $\mu$ are the complex Lamé constants (N/m²), $\rho$ is the density (kg/m³), $\circ$ denotes a vector dot product; u is the Cartesian coordinate displacement vector of the material and $\partial$ is the partial differential.

Figure 2:
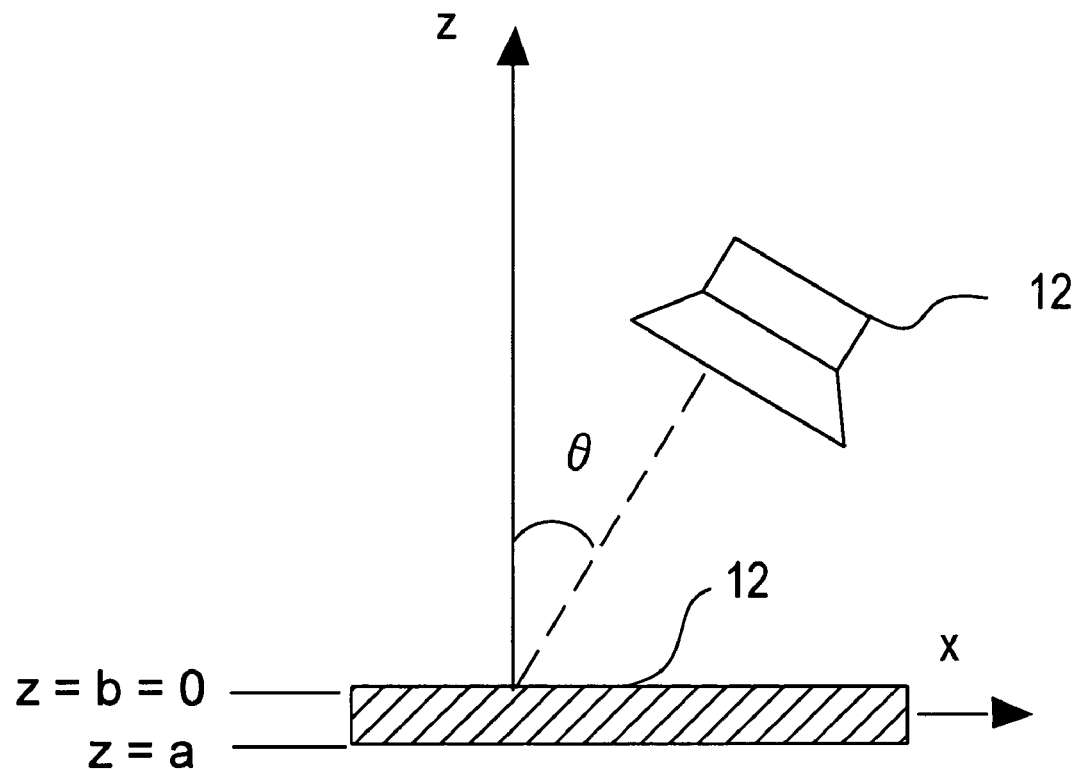
FIG. 2 depicts the coordinate system of the test setup of FIG. 1.

The coordinate system of the test configuration is shown in FIG. 2. Note that using this orientation results in b=0 and a having a value less than zero. The thickness h of the specimen 10 is a positive value. Equation (1) is manipulated by writing the displacement vector u as $$u = \begin{Bmatrix} u_x(x, y, z, t) \\ u_y(x, y, z, t) \\ u_z(x, y, z, t) \end{Bmatrix}, \tag{2}$$

where x is the location along the specimen 10, y is the location into the specimen 10, and z is the location normal to the specimen 10 and t is time (s). The symbol $\nabla$ is the gradient vector differential operator written in three-dimensional Cartesian coordinates as $$\nabla = \frac{\partial}{\partial x} i_x + \frac{\partial}{\partial y} i_y + \frac{\partial}{\partial z} i_z, \tag{3}$$

with $i_x$ denoting the unit vector in the x-direction, $i_y$ denoting the unit vector in the y-direction, and $i_z$ denoting the unit vector in the z-direction; $\nabla^2$ is the three-dimensional Laplace operator operating on vector u as $$\nabla^2 u = \nabla^2 u_x i_x + \nabla^2 u_y i_y + \nabla^2 u_z i_z, \tag{4}$$

with $\nabla^2$ operating on scalar u as $$\nabla^2 u_{x,y,z} = \nabla \cdot \nabla u_{x,y,z} = \frac{\partial^2 u_{x,y,z}}{\partial x^2} + \frac{\partial^2 u_{x,y,z}}{\partial y^2} + \frac{\partial^2 u_{x,y,z}}{\partial z^2}; \tag{5}$$

and the term $\nabla \cdot u$ is called the divergence and is equal to $$\nabla \cdot u = \frac{\partial u_x}{\partial x} + \frac{\partial u_y}{\partial y} + \frac{\partial u_z}{\partial z}. \tag{6}$$

The displacement vector u is written as $$u = \nabla \phi + \nabla \times \vec{\psi}, \tag{7}$$

where $\phi$ is a dilatational scalar potential, x denotes a vector cross product, and $\vec{\psi}$ is an equivoluminal vector potential expressed as $$\vec{\psi} = \begin{Bmatrix} \psi_x(x, y, z, t) \\ \psi_y(x, y, z, t) \\ \psi_z(x, y, z, t) \end{Bmatrix}. \tag{8}$$

The problem is formulated as a two-dimensional system, thus y=0, $u_y(x,y,z,t)$=0, and $\partial(\cdot)/\partial_y$=0. Expanding equation (7) and breaking the displacement vector into its individual nonzero terms yields $$u_x(x, z, t) = \frac{\partial \phi(x, z, t)}{\partial x} - \frac{\partial \psi_y(x, z, t)}{\partial z} \text{ and} \quad (9)$$

$$u_z(x, z, t) = \frac{\partial \phi(x, z, t)}{\partial z} + \frac{\partial \psi_y(x, z, t)}{\partial x}. \quad (10)$$

Equations (9) and (10) are next inserted into equation (1), which results in $$c_d^2 \nabla^2 \phi(x, z, t) = \frac{\partial^2 \phi(x, z, t)}{\partial t^2} \text{ and} \quad (11)$$

$$c_s^2 \nabla^2 \psi_y(x, z, t) = \frac{\partial^2 \psi_y(x, z, t)}{\partial t^2} \quad (12)$$

where equation (11) corresponds to the dilatational component and equation (12) corresponds to the shear component of the displacement field. Correspondingly, the constants $c_d$ and $c_s$ are the complex dilatational and shear wave speeds, respectively, and are determined by $$c_d = \sqrt{\frac{\lambda + 2\mu}{\rho}} \text{ and} \quad (13)$$

$$c_s = \sqrt{\frac{\mu}{\rho}}. \quad (14)$$

The relationship of the Lamé constants to the Young's and shear moduli is shown as $$\lambda = \frac{E\upsilon}{(1+\upsilon)(1-2\upsilon)} \text{ and} \quad (15)$$

$$\mu = G = \frac{E}{2(1+\upsilon)}, \quad (16)$$

where E is the complex Young's modulus (N/m$^2$), G is the complex shear modulus (N/m$^2$), and $\upsilon$ is the Poisson's ratio of the material (dimensionless).

The conditions of infinite length and steady-state response are now imposed, allowing the scalar and vector potential to be written as $$\phi(x,z,t) = \Phi(z)\exp(ikx)\exp(i\omega t) \quad (17)$$

and $$\psi_y(x,z,t) = \Psi(z)\exp(ikx)\exp(i\omega t) \quad (18)$$

where i is the square root of −1, $\omega$ is frequency (rad/s), and k is wavenumber with respect to the x axis (rad/m), $\Phi$ is the amplitude of the scalar potential ø as a function of z and $\Psi$ is the amplitude of the vector potential as a function of z. Inserting equation (17) into equation (11) yields $$\frac{d^2 \Phi(z)}{dz^2} + \alpha^2 \Phi(z) = 0, \quad (19)$$

where $\alpha$ is the modified dilatational wavenumber and d is the differential operator and where $$\alpha = \sqrt{k_d^2 - k^2}, \quad (20)$$

with $k_d$ is the actual dilatational wave number and $$k_d = \frac{\omega}{c_d}. \quad (21)$$

Inserting equation (18) into equation (12) yields $$\frac{d^2 \Psi(z)}{dz^2} + \beta^2 \Psi(z) = 0, \quad (22)$$

where $$\beta = \sqrt{k_1^2 - k^2}, \quad (23)$$

with $\beta$ as the modified shear wavenumber and $$k_s = \frac{\omega}{c_s}. \quad (24)$$

The solution to equation (19) is $$\Phi(z) = A(k,\omega)\exp(i\alpha z) + B(k,\omega)\exp(-i\alpha z), \quad (25)$$

and the solution to equation (22) is $$\Psi(z) = C(k,\omega)\exp(i\beta z) + D(k,\omega)\exp(-i\beta z), \quad (26)$$

where A(k,$\omega$), B(k,$\omega$), C(k,$\omega$), and D(k,$\omega$) are wave response coefficients that are determined below. The displacements can now be written as functions of the unknown constants using the expressions in equations (9) and (10). They are $$\begin{aligned} u_z(x, z, t) &= U_z(k, z, \omega)\exp(ikx)\exp(i\omega t) \\ &= \{i\alpha[A(k, \omega)\exp(i\alpha z) - B(k, \omega)\exp(-i\alpha z)] + \\ &\quad ik[C(k, \omega)\exp(i\beta z) + \\ &\quad D(k, \omega)\exp(-i\beta z)]\}\exp(ikx)\exp(i\omega t), \end{aligned} \quad (27)$$

with $U_z$ as the amplitude of displacement in the "z" direction and $$\begin{aligned} u_x(x, z, t) &= U_x(k, z, \omega)\exp(ikx)\exp(i\omega t) \\ &= \{ik[A(k, \omega)\exp(i\alpha z) + B(k, \omega)\exp(-i\alpha z)] - \\ &\quad i\beta[C(k, \omega)\exp(i\beta z) - D(k, \omega)\exp(-i\beta z)]\} \\ &\quad \exp(ikx)\exp(i\omega t) \end{aligned} \quad (28)$$

with $U_x$ as the amplitude of displacement in the "x" direction. The normal stress at the top of the plate (z=b) is equal to opposite the pressure load created by the projector. This expression is $$\tau_{zz}(x, b, t) = (\lambda + 2\mu)\frac{\partial u_z(x, b, t)}{\partial z} + \lambda\frac{\partial u_x(x, b, t)}{\partial x} = -p_0(x, b, t), \quad (29)$$

and the tangential stress at the top of the plate b is zero and this equation is written as $$\tau_{zx}(x, b, t) = \mu\left[\frac{\partial u_x(x, b, t)}{\partial z} + \frac{\partial u_z(x, b, t)}{\partial x}\right] = 0. \quad (30)$$

The normal stress the bottom of the plate (z=a) is equal to zero. This expression is $$\tau_{zz}(x, a, t) = (\lambda + 2\mu)\frac{\partial u_z(z, a, t)}{\partial z} + \lambda\frac{\partial u_x(x, a, t)}{\partial x} = 0, \quad (31)$$

and the tangential stress at the bottom of the plate is zero and this equation is written as $$\tau_{zx}(x, a, t) = \mu\left[\frac{\partial u_x(x, a, t)}{\partial z} + \frac{\partial u_z(x, a, t)}{\partial x}\right] = 0. \quad (32)$$

The applied load in equation (29) is an acoustic pressure and is modeled as a function at definite wavenumber and frequency as $$p_0(x,z,t) = P_0(\omega)\exp(ikx)\exp(i\omega t), \quad (33)$$

with P being the amplitude and where the wavenumber k is found using $$k = \frac{\omega}{c_f}\sin(\theta), \quad (34)$$

where $c_f$ is the compressional wavespeed of air (m/s) and $\theta$ is the angle of incidence of the projector with the z axis (rad).

Assembling equations (1)–(34) and letting b=0 yields the "A" matrix, x vector, and b vector in a four-by-four system of linear equations that model the system written in matrix form. They are $$Ax=b; \ (A \ 4\times4, \ x \ 4\times1, \ b \ 4\times1) \quad (35)$$

where the entries of equation (35) are $$A_{11} = -\alpha^2\lambda - 2\alpha^2\mu - \lambda k^2, \quad (36)$$

$$A_{12} = A_{11}, \quad (37)$$

$$A_{13} = 2k\beta\mu, \quad (38)$$

$$A_{14} = A_{13}, \quad (39)$$

$$A_{21} = -2\mu k\alpha, \quad (40)$$

$$A_{22} = -A_{21}, \quad (41)$$

$$A_{23} = \mu\beta^2 - \mu k^2, \quad (42)$$

$$A_{24} = A_{23}, \quad (43)$$

$$A_{31}A_{11}\exp(i\alpha a), \quad (44)$$

$$A_{32} = A_{11}\exp(-i\alpha a), \quad (45)$$

$$A_{33} = -A_{13}\exp(i\beta a), \quad (46)$$

$$A_{34} = A_{13}\exp(-i\beta a), \quad (47)$$

$$A_{41} = A_{21}\exp(i\alpha a), \quad (48)$$

$$A_{42} = -A_{21}\exp(-i\alpha a), \quad (49)$$

$$A_{43} = A_{23}\exp(i\beta a), \quad (50)$$

$$A_{44} = A_{23}\exp(-i\beta a), \quad (51)$$

$$b_{11} = -P_0(\omega), \quad (52)$$

$$b_{21} = 0, \quad (53)$$

$$b_{31} = 0, \quad (54)$$

and $$b_{41} = 0. \quad (55)$$

Using equations (35)–(55) the solution to the constants $A(k,\omega)$, $B(k,\omega)$, $C(k,\omega)$, and $D(k,\omega)$ can be calculated at each specific wavenumber and frequency using $$x = A^{-1}b. \quad (56)$$

Once these are known, the transfer function T between the wall motion in the z direction at z=a and the wall motion in the z direction at z=b is now written in closed form notation using equations (27) and (56). The resulting expression is $$T(k, \omega) = \frac{U_z(k, a, \omega)}{U_z(k, b, \omega)} = \frac{4\alpha\beta k^2\sin(\alpha h) + (\beta^2 - k^2)^2\sin(\beta h)}{4\alpha\beta k^2\sin(\alpha h)\cos(\beta h) + (\beta^2 - k^2)^2\cos(\alpha h)\sin(\beta h)}. \quad (57)$$

The first step is to solve for the response at zero wavenumber, or what is typically referred to as broadside response, to determine the dilatational wavespeed. At zero wavenumber, the angle between the direction of propagation of the insonification energy and the z axis is zero. The response of the structure to broadside energy is comprised entirely of dilatational waves, i.e., no shear waves are excited at zero wavenumber. Furthermore, the transfer function given in equation (57) reduces to $$T(0, \omega) = \frac{1}{\cos(\alpha_1 h)} = T_1 = \frac{1}{R_1}, \quad (58)$$

where $T_1$ (or $R_1$) is the measurement data from the experiment with a insonification angle of zero and is typically a frequency-dependent complex number and the subscript 1 denotes the first experiment. Equation (58) can be expanded into real and imaginary parts and solved, resulting in a value for $\alpha_1$ at every frequency in which a measurement is made. The solution to the real part Re of $\alpha_1$ is $$\text{Re}(\alpha_1) = \begin{cases} \frac{1}{2h}\text{Arccos}(s) + \frac{n\pi}{2h} & n \text{ even} \\ \frac{1}{2h}\text{Arccos}(-s) + \frac{n\pi}{2h} & n \text{ odd,} \end{cases} \quad (59)$$

where $$s = [Re(R_1)]^2 + [Im(R_1)]^2 - \sqrt{\{[Re(R_1)]^2 + [Im(R_1)]^2\}^2 - \{2[Re(R_1)]^2 - 2[Im(R_1)]^2 - 1\}}, \quad (60)$$

and n is a non-negative integer and the capital A denotes the principal value of the inverse cosine function. The value of n is determined from the function s, which is a periodically varying cosine function with respect to frequency. At zero frequency, n is 0. Every time s cycles through $\pi$ radians (180 degrees), n is increased by 1. When the solution to the real part of $\alpha_1$ is found, the solution to the imaginary part Im of $\alpha_1$ is then written as $$\text{Im}(\alpha_1) = \frac{1}{h} \log_e \left\{ \frac{Re(R_1)}{\cos[Re(\alpha_1)h]} - \frac{Im(R_1)}{\sin[Re(\alpha_1)h]} \right\}. \quad (61)$$

The real and imaginary parts of $\alpha_1$ from equations (59) and (61) respectively are combined to yield the complex wavenumber. Because this measurement is made at zero wavenumber (k=0), this is equal to the dilatational wavenumber. Thus, the dilatational wavespeed is equal to $$c_d = \frac{\omega}{[Re(\alpha_1) + i\,Im(\alpha_1)]}. \quad (62)$$

To solve for the shear wavespeed, the specimen must be excited at a nonzero wavenumber. This is done next.

The next step is to solve for the response at nonzero wavenumber to determine the shear wavespeed. At nonzero wavenumber, the transfer function is given in equation (57). For this nonzero angle of insonification, this can be expressed as $$T(k,\omega) = \frac{4\alpha_2\beta_2 k_2^2 \sin(\alpha_2 h) + (\beta_2^2 - k_2^2)^2 \sin(\beta_2 h)}{4\alpha_2\beta_2 k_2^2 \sin(\alpha_2 h)\cos(\beta_2 h) + (\beta_2^2 - k_2^2)^2 \cos(\alpha_2 h)\sin(\beta_2 h)} = T_2 = \frac{1}{R_2}, \quad (63)$$

where $T_2$ (or $R_2$) is the measurement data from the experiment at nonzero insonification angle and is typically a frequency-dependent complex number and the subscript 2 denotes the second angle or experiment. It is noted that $\alpha_2$ in equation (63) is different from $\alpha_1$ in equation (58). This difference is based on a $k^2$ term shown in equation (20) where the wavenumber $\alpha$ is defined. Due to the complexity of equation (63), there is no simple method to rewrite the equation as a function f of $\beta_2$, the variable that is to be estimated. Equation (63) can be rewritten as $$f(\beta_2) = 0 = 4\alpha_2\beta_2 k_2^2 \sin(\alpha_2 h)[\cos(\beta_2 h) - R_2] + (\beta_2^2 - k_2^2)^2 \sin(\beta_2 h)[\cos(\alpha_2 h) - R_2], \quad (64)$$

where the problem now becomes finding the zeros of the right hand side of equation (64), or in the presence of actual data that contains noise, finding the relative minima of the right hand side of equation (64) and determining which relative minimum corresponds to shear wave propagation and which relative minima are extraneous. Because equation (64) has a number of relative minima, zero finding algorithms are not applied to this function, as they typically do not find all of the minima locations. The best method to find all of the minima locations is by plotting the absolute value of the right hand side of equation (64) as a surface with the real part of $\beta_2$ on one axis and the imaginary part of $\beta_2$ on the other axis. The value $\alpha_2$ is determined using $$\alpha_2 = \sqrt{k_d^2 - k_2^2} = \sqrt{\alpha_1^2 - k_2^2}, \quad (65)$$

so that equation (64) is a function of only $\beta_2$. Once this function is plotted, the minima can be easily identified and the corresponding value of $(\beta_2)_m$ at the location of the minima can be determined by examination of the minimum location, sometimes referred to as the grid method. The shear wave speed(s) are then determined using $$(k_s)_m = \sqrt{(\beta_2)_m^2 + k_2^2} \quad (66)$$

and $$(c_s)_m = \frac{\omega}{(k_s)_m} \quad (67)$$

where the subscript m denotes each minima value that was found by inspecting the surface formed from equation (64). The determination of the correct index of m that corresponds to shear wave propagation is done below.

The material properties such as Young's modulus and other material properties can be determined from the wavespeeds. The Lamé constants are calculated with equations (13) and (14) written as $$\mu_m = \rho(c_s)_m^2 \quad (68)$$

and $$\lambda_m = \rho c_d^2 \rho(c_s)_m^2. \quad (69)$$

To determine the correct index m that corresponds to the actual wave propagation rather than an extraneous solution, a third set of measurements are made at a nonzero incidence angle that is not equal to the angle used previously. The model in equation (63) is calculated from the estimated material properties and a residual value is determined using the third set of measurements. Each m indexed residual at a specific frequency is defined as $$(\varepsilon_3)_m = \frac{4\alpha_3(\beta_3)_m k_3^2 \sin(\alpha_3 h) + [(\beta_3)_m^2 - k_3^2]^2 \sin[(\beta_3)_m h]}{4\alpha_3(\beta_3)_m k_3^2 \sin(\alpha_3 h)\cos[(\beta_3)_m h] + [(\beta_3)_m^2 - k_3^2]^2 \cos(\alpha_3 h)\sin[(\beta_3)_m h]} - \frac{1}{R_3}, \quad (70)$$

where $$\alpha_3 = \sqrt{k_d^2 - k_3^2} = \sqrt{\alpha_1^2 - k_3^2} \quad (71)$$

and $$(\beta_3)_m = \sqrt{(\beta_2)_m^2 + k_2^2 - k_3^2}, \quad (72)$$

and the subscript 3 denotes the third experiment. The smallest residual value corresponds to the correct value of index m and the correct values of Lamé constants. Poisson's ratio is then calculated using $$\nu = \frac{\lambda}{2(\mu+\lambda)}. \quad (73)$$

Young's modulus can be calculated with $$E = \frac{2\mu(2\mu+3\lambda)}{2(\mu+\lambda)} \quad (74)$$

and the shear modulus can be determined using $$G = \mu. \quad (75)$$

The above measurement method can be simulated by means of a numerical example. Soft rubber-like material properties are used in this simulation. The material has a Young's modulus E of $[(1e8-i2e7)+(5e3f-i3e2f)]$ N/m² where f is frequency in Hz, Poisson's ratio $\nu$ is equal to 0.40 (dimensionless), density $\rho$ is equal to 1200 kg/m³, and a thickness h of 0.01 m. A compressional (acoustic) wave velocity of $c_f$ of 343 m/s for air is used. All other parameters can be calculated from these values. The insonification angles of zero, twenty, and forty degrees are chosen to illustrate this method.

Figure 3:
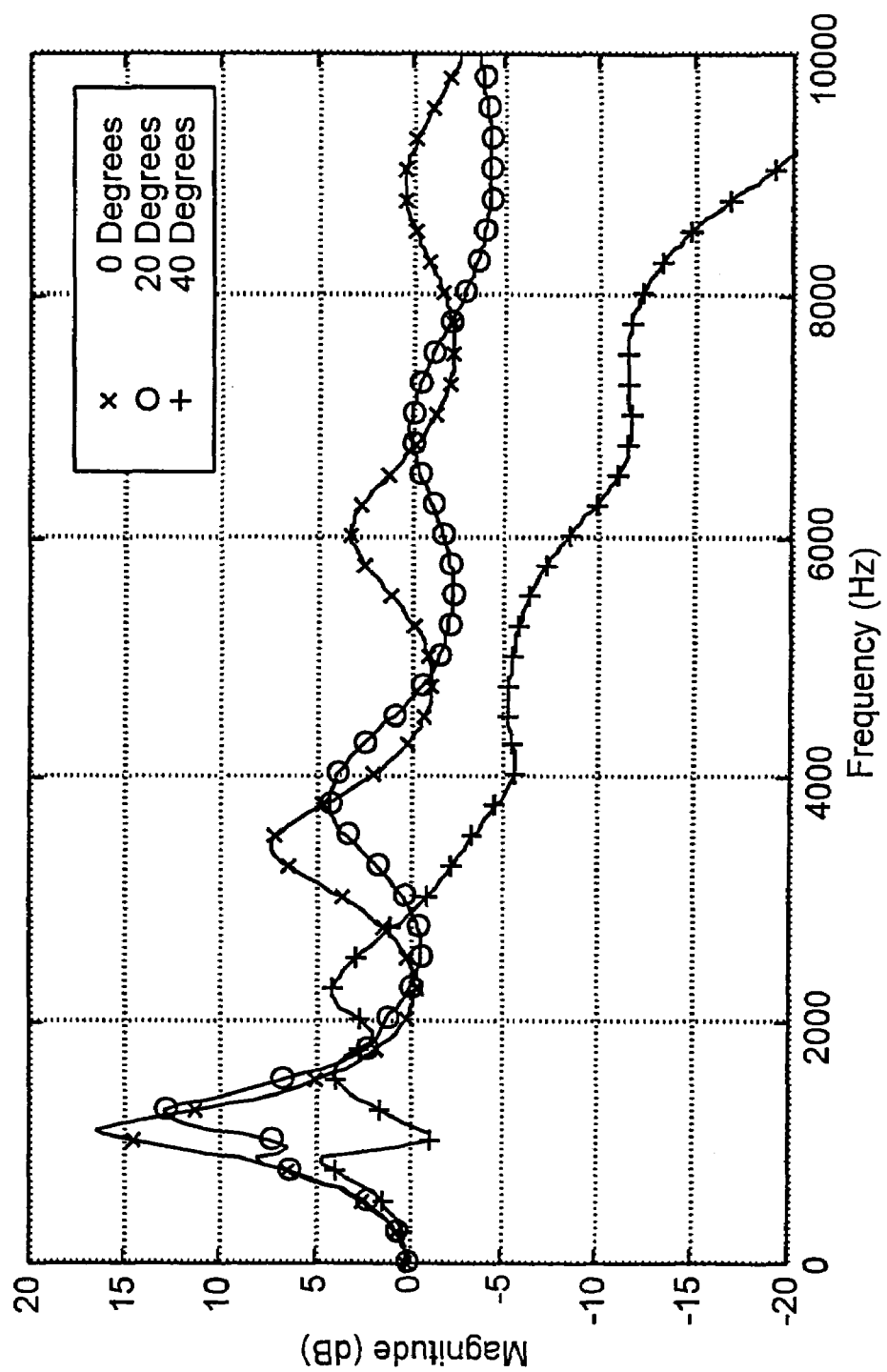
FIG. 3 is a plotted graph depicting the measurable transfer function of magnitude versus the frequency.
Figure 4:
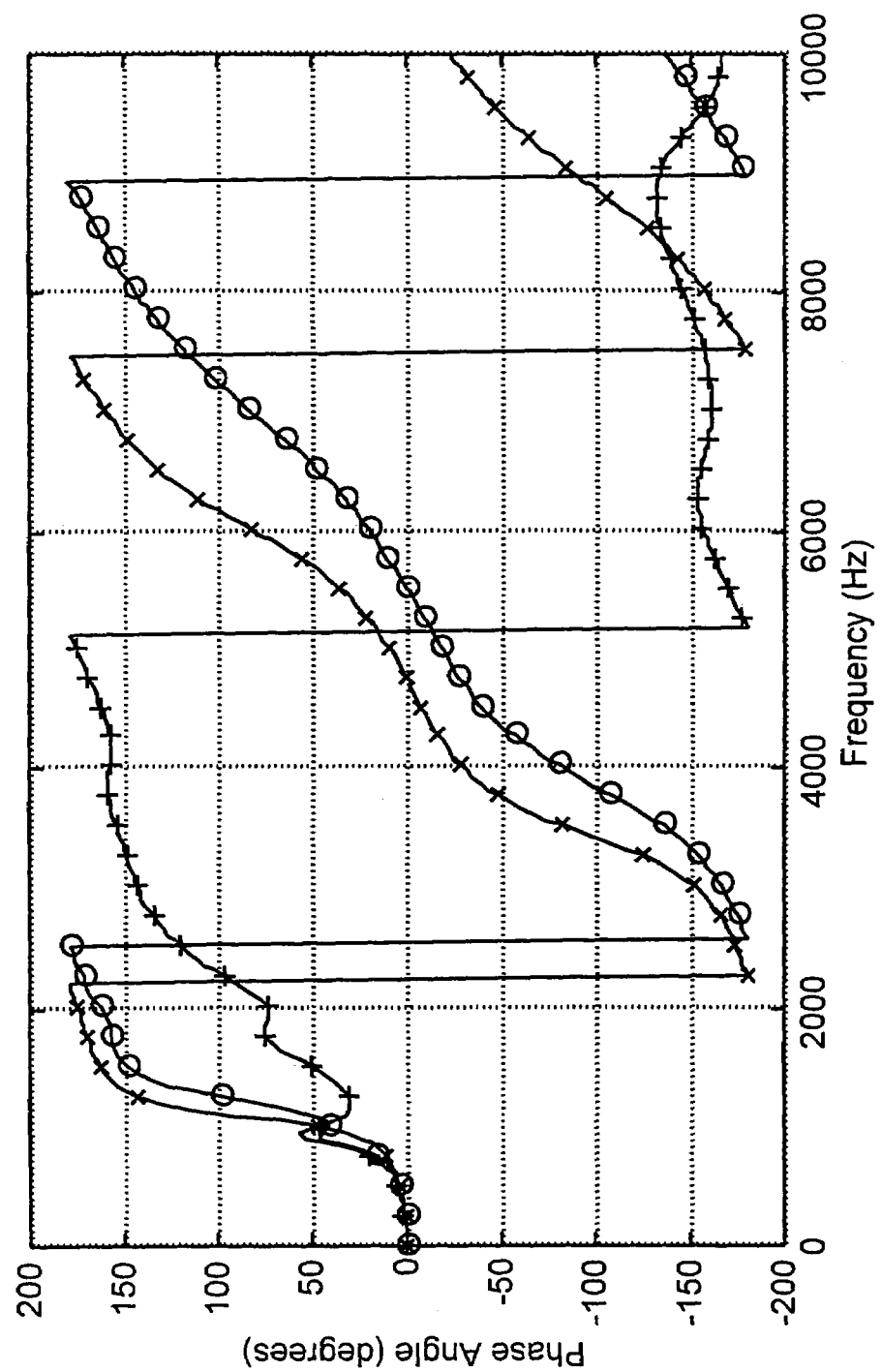
FIG. 4 is a plotted graph depicting the measurable transfer function of phase angle versus the frequency.

FIGS. 3 and 4 are plots of the transfer functions of equation (57) at zero (x symbol), twenty (o symbol), and forty degree (+ symbol) insonification angles versus the frequency.

FIG. 3 represents the magnitude of the transfer function versus the frequency and FIG. 4 represents the phase angle versus the frequency.

Figure 5:
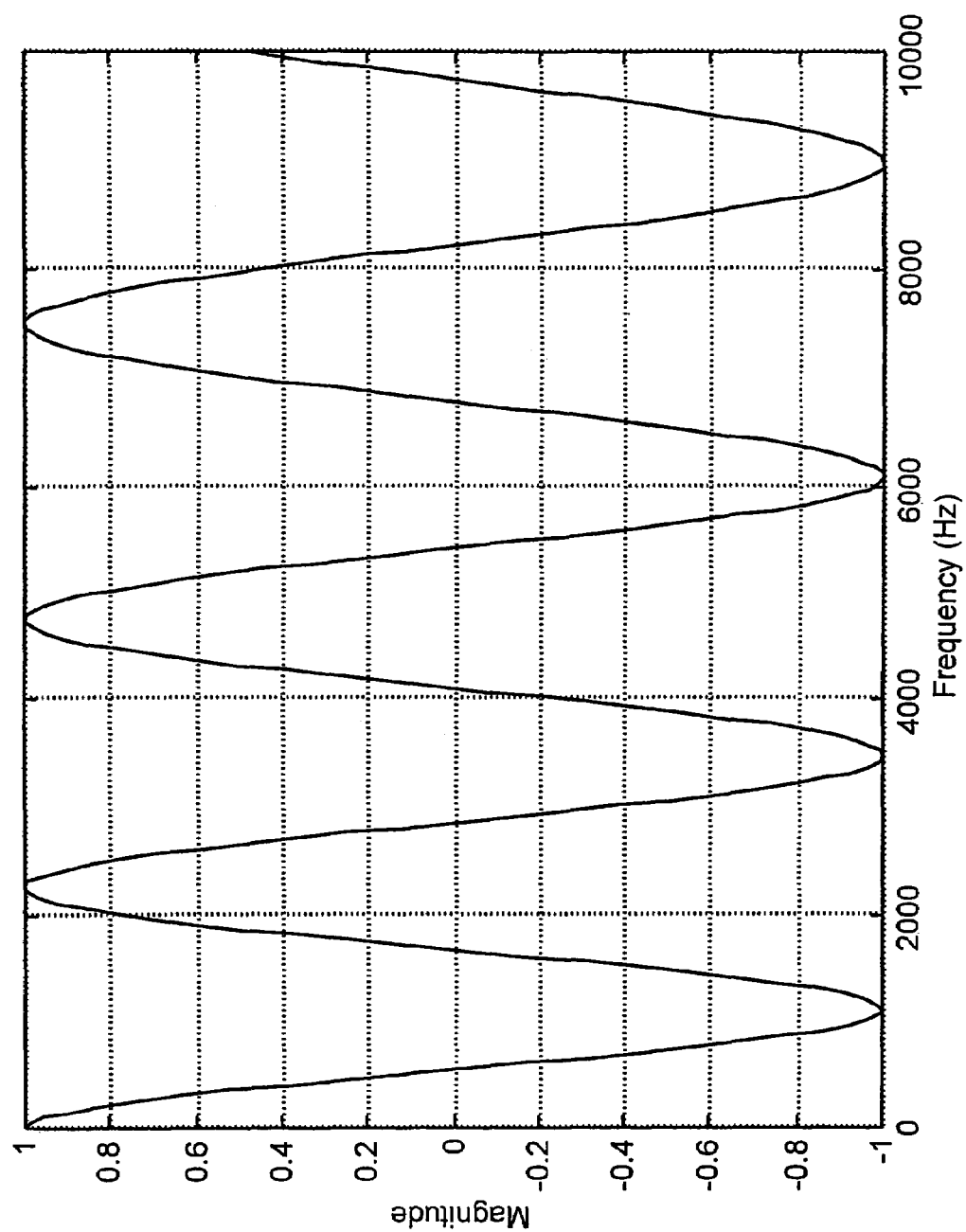
FIG. 5 is a plotted graph depicting the measurable transfer function "s" versus the frequency.
Figure 6:
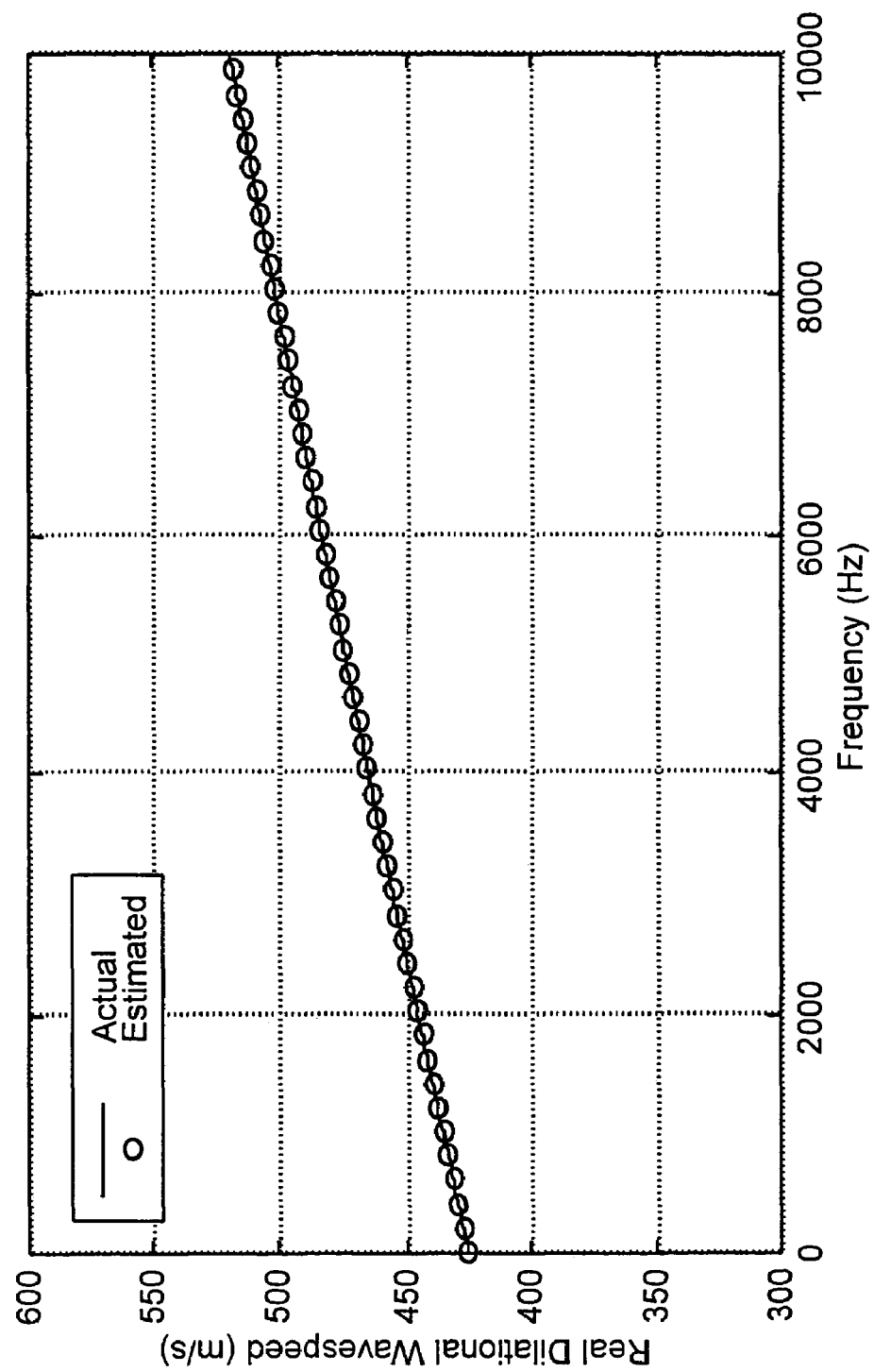
FIG. 6 is a plotted graph depicting the real component of the actual and estimated dilatational wavespeed versus the frequency.
Figure 7:
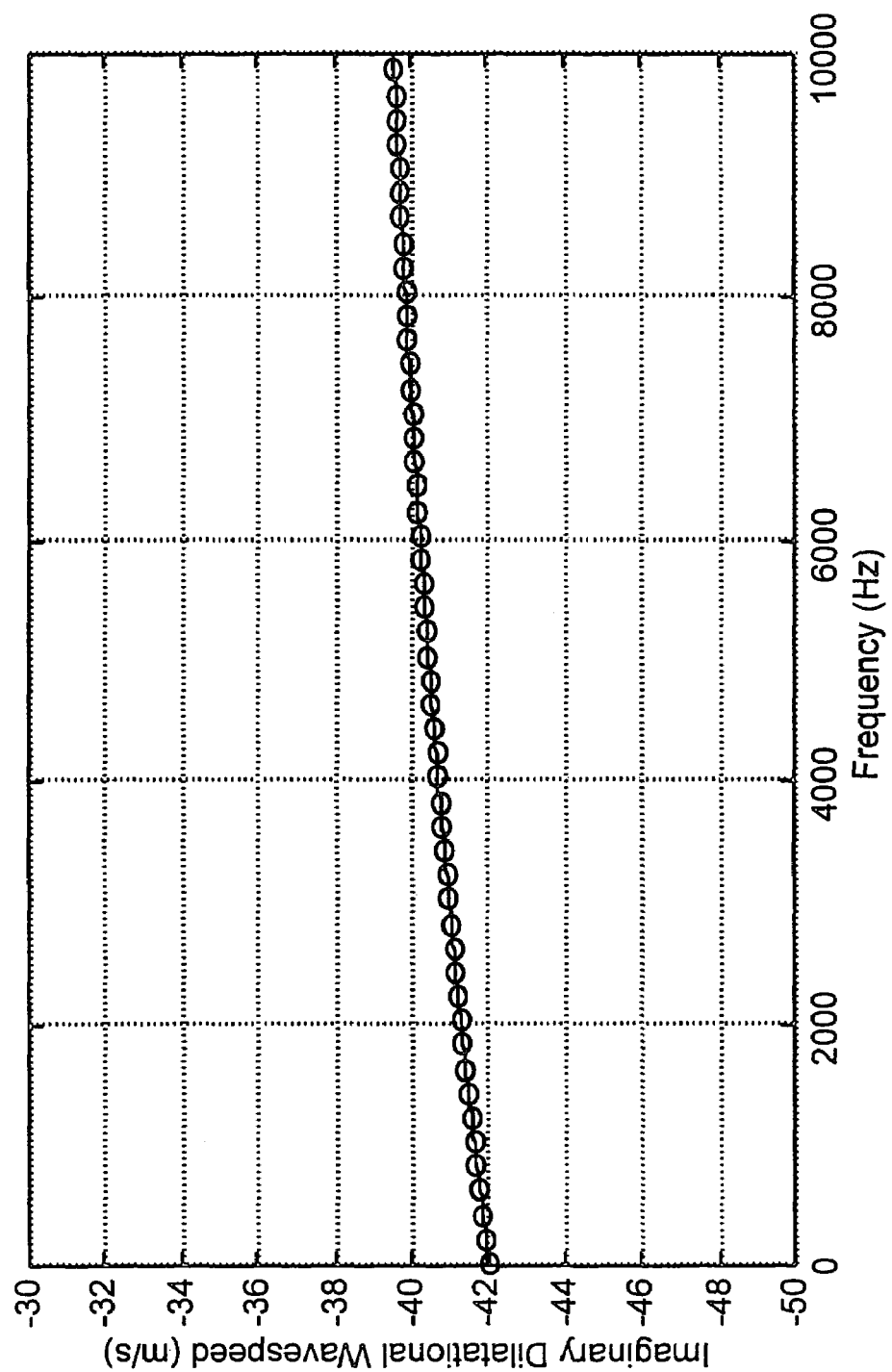
FIG. 7 is a plotted graph depicting the imaginary component of the actual and estimated dilatational wavespeed versus the frequency.

Once the transfer functions are known (typically by measurement but here by numerical simulation), the dilatational wavespeed can be estimated using equations (59)–(62). FIG. 5 is a plot of the function s versus the frequency. FIGS. 6 and 7 are plots of the actual dilatational wavespeed (solid line) and the estimated dilatational wavespeed (o symbol) versus the frequency. FIG. 6 depicts the real component and FIG. 7 depicts the imaginary component.

Figure 8:
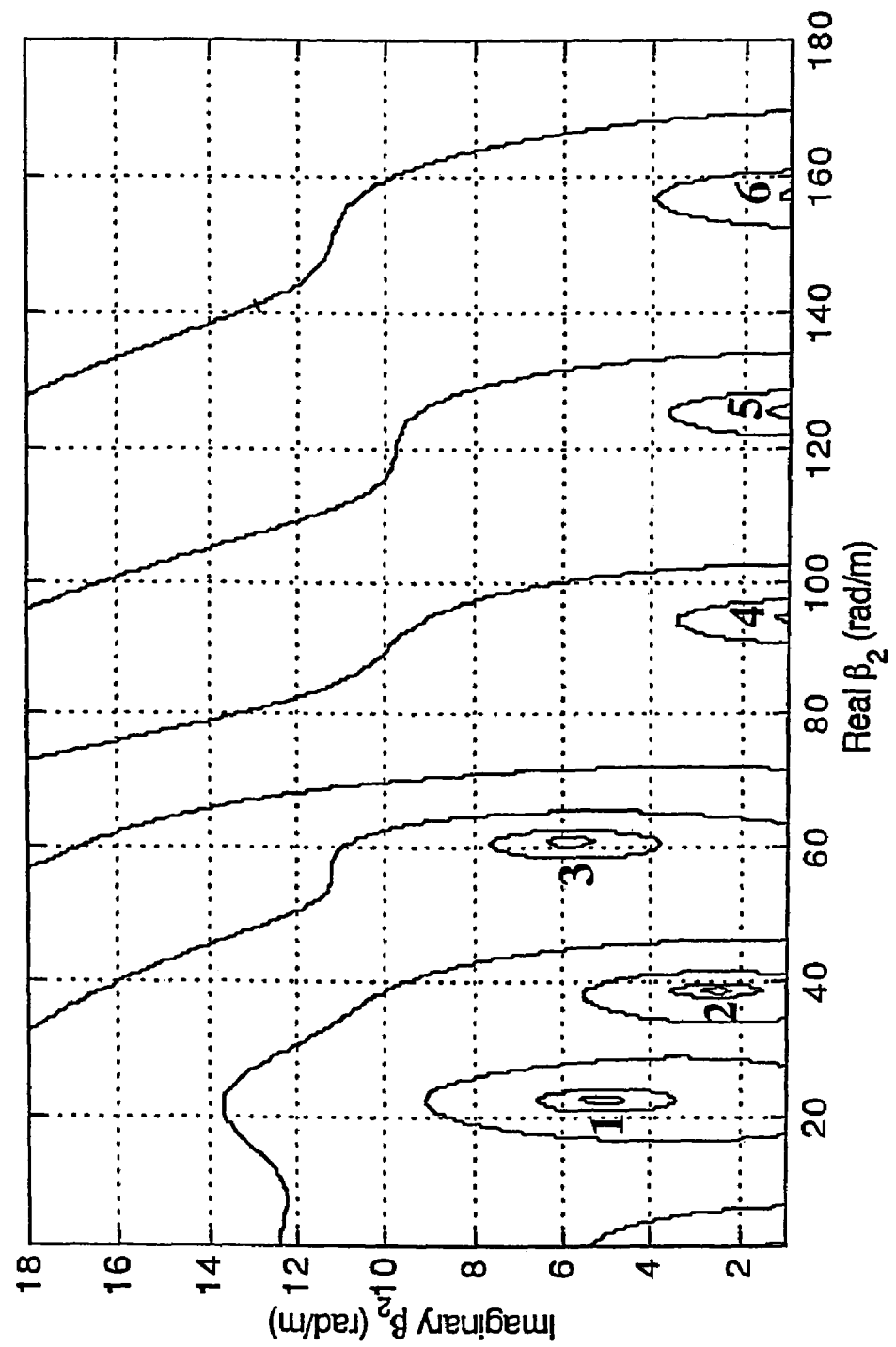
FIG. 8 is a plotted graph depicting the contour of the surface versus both the real and imaginary parts of $\beta_2$.

FIG. 8 is a plot of the surface defined in equation (64) versus real and imaginary components of $\beta_2$ at 1800 Hz. FIG. 8 depicts a contour plot of the surface versus both the real and imaginary parts of $\beta_2$. For the figure, there are six distinct local minima that are labeled in bold numbers. The seventh local minima corresponds to $\beta_2=0$ which implies there is no shear wave propagation; a physically unrealizable condition at nonzero wavenumber. These six local minima are processed at a third measurement location according to equation (70). The results are listed in Table 1. Local minimum number 3 has the smallest residual value and corresponds to the shear wave propagation. The value for $(\beta_2)_3$ is equal to 61.3+5.9i compared to the actual value of $\beta_2$ which is 61.0+5.9i. The small difference between the two values can be attributed to discritization of the surface.

TABLE 1

Values of $(\beta_2)_m$ and $(\epsilon_3)_m$ at the Local Minima

| Local Minima Number m | Value of $(\beta_2)_m$ | Residual $(\epsilon_3)_m$ (Equation (70)) |
|---|---|---|
| 1 | 22.6 + 5.2i | 0.257 |
| 2 | 38.8 + 2.5i | 2.064 |
| 3 | 61.3 + 5.9i | 0.013 |
| 4 | 94.5 + 1.1i | 0.426 |
| 5 | 125.1 + 1.0i | 0.326 |
| 6 | 157.5 + 1.1i | 0.349 |

Figure 9:
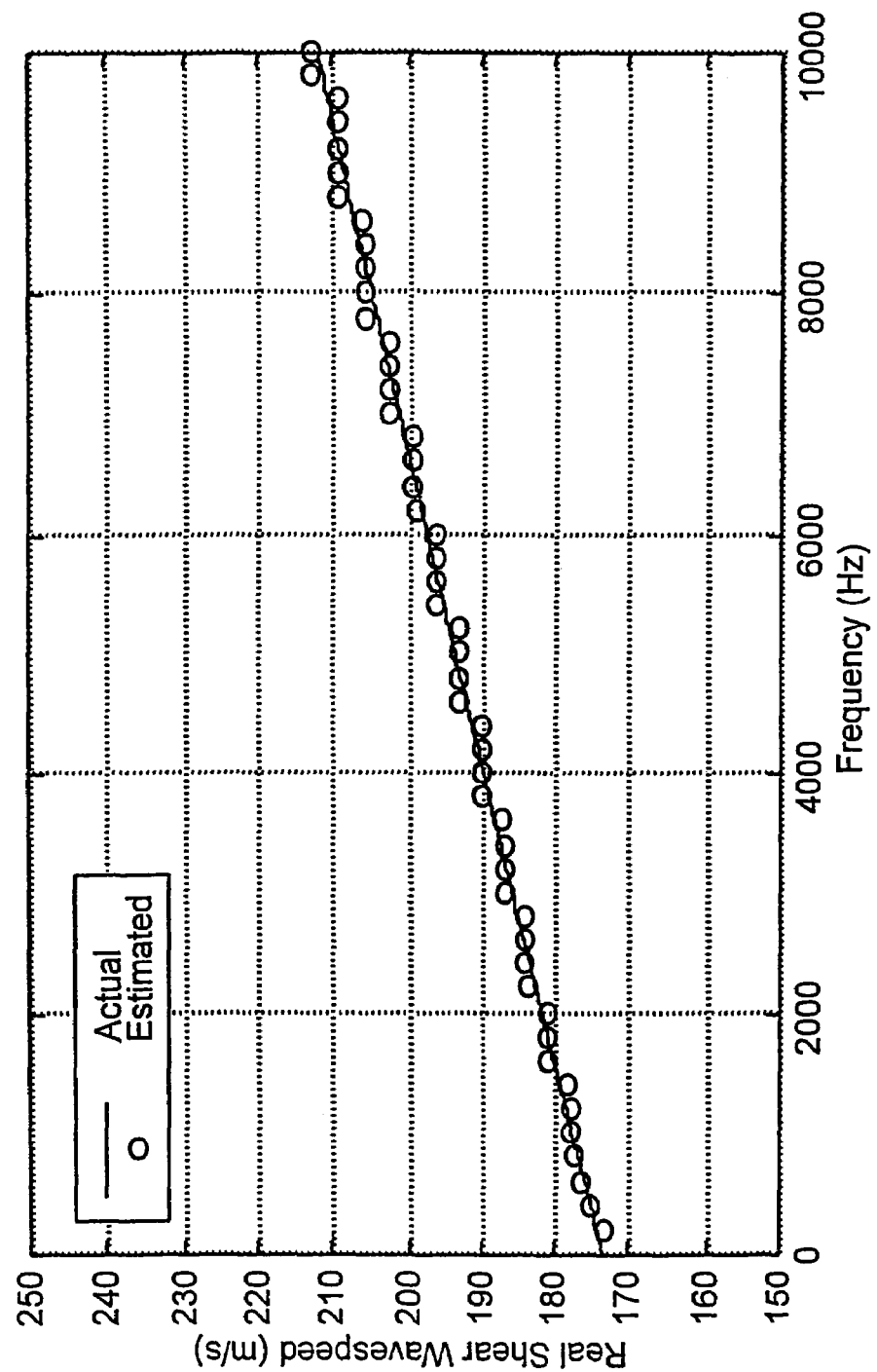
FIG. 9 is a plotted graph depicting the actual shear wavespeed and the estimated shear wavespeed versus the frequency with the real component.
Figure 10:
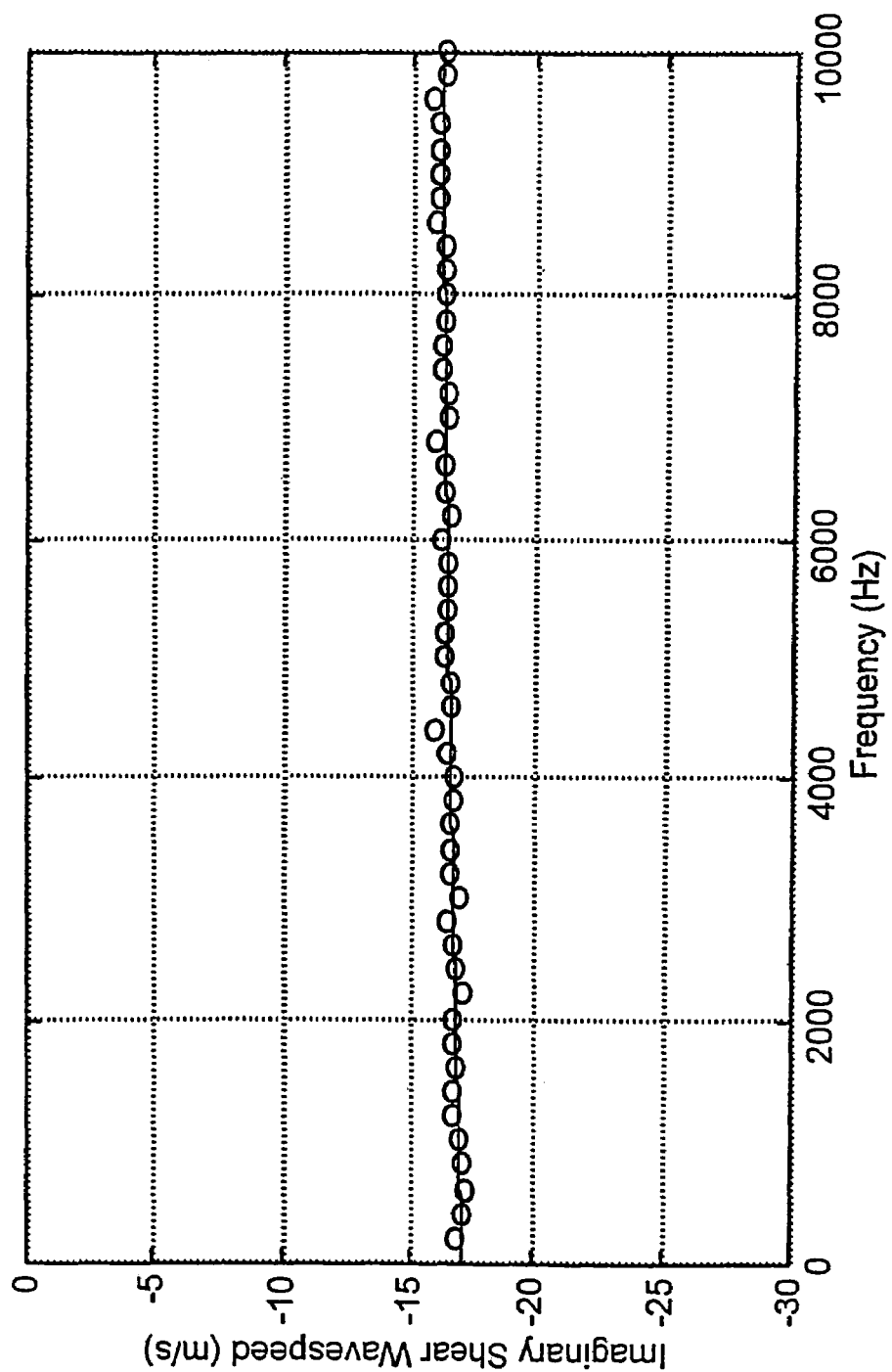
FIG. 10 is a plotted graph depicting the actual shear wavespeed and the estimated shear wavespeed versus the frequency with the imaginary component.

FIGS. 9 and 10 are plots of the actual shear wavespeed (solid line) and the estimated shear wavespeed (o symbol) versus the frequency. FIG. 9 depicts the real component and FIG. 10 depicts the imaginary component. As in FIG. 8, the small difference between the two values can be attributed to discritization of the surface.

Figure 11:
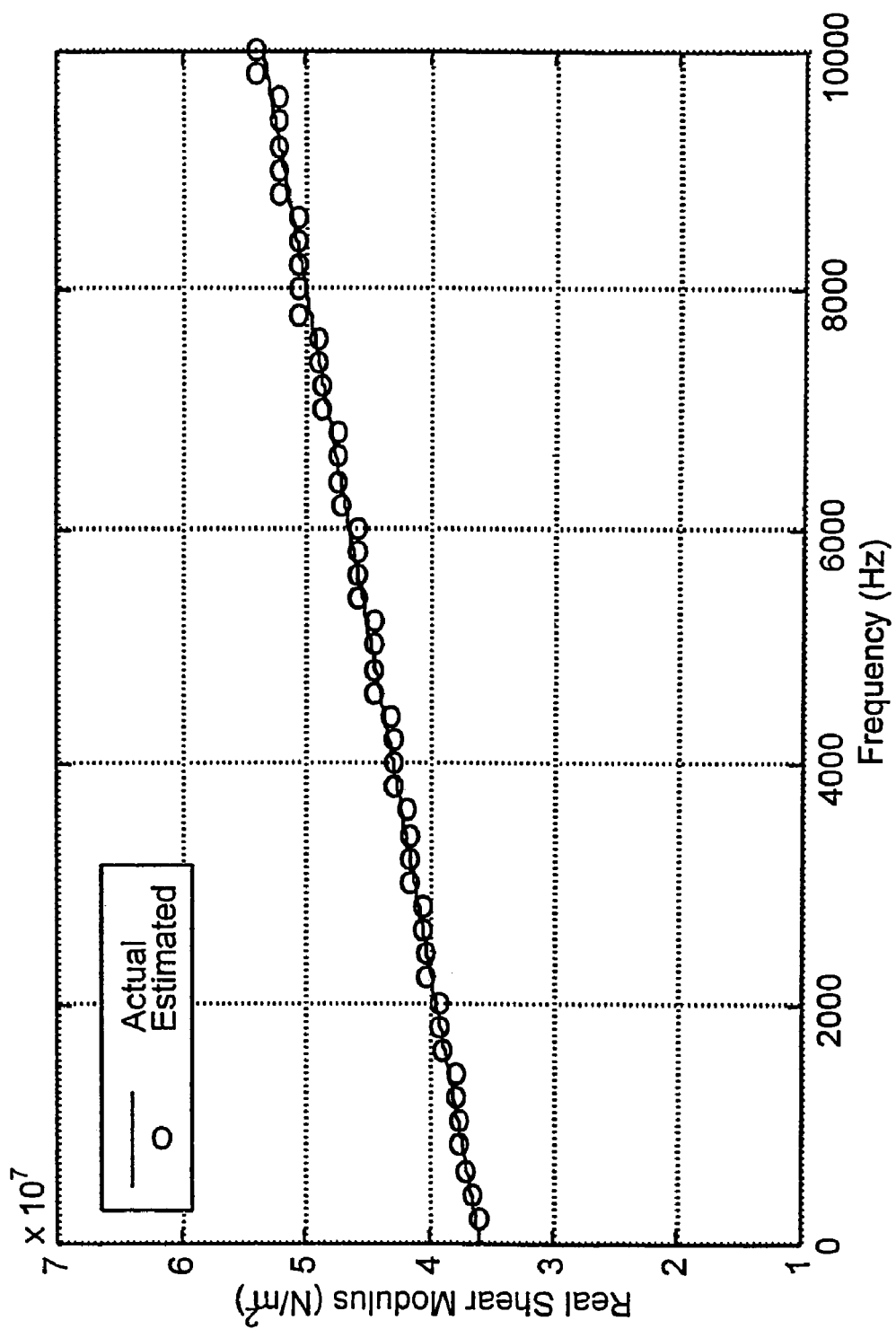
FIG. 11 is a plotted graph depicting the actual shear modulus and the estimated shear modulus versus the frequency with the real component.
Figure 12:
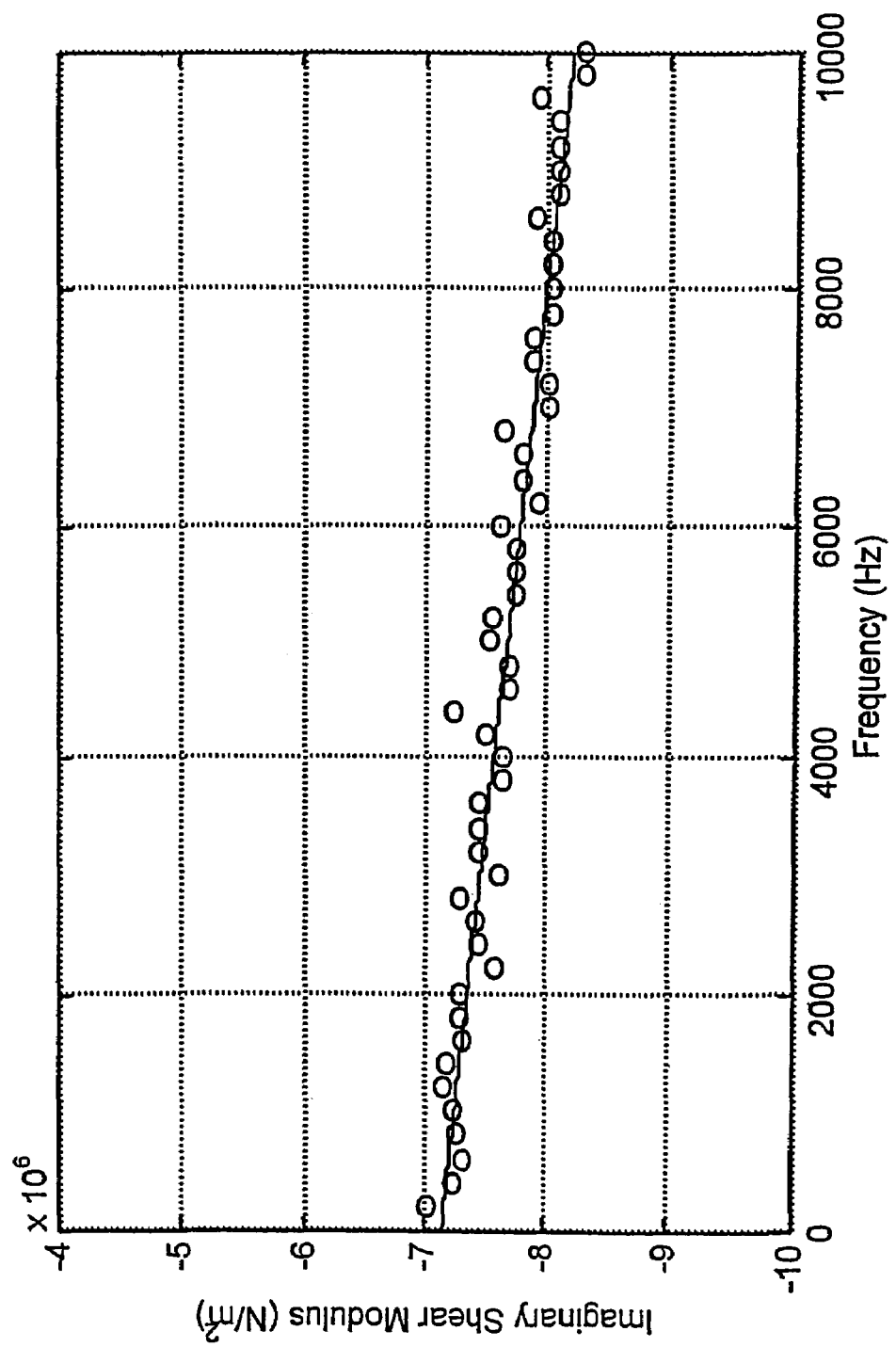
FIG. 12 is a plotted graph depicting the actual shear modulus and the estimated shear modulus versus the frequency with the imaginary component.

FIGS. 11 and 12 are plots of the actual shear modulus (solid line) and the estimated shear modulus (o symbol) versus the frequency. FIG. 11 depicts the real component and FIG. 12 depicts the imaginary component.

Figure 13:
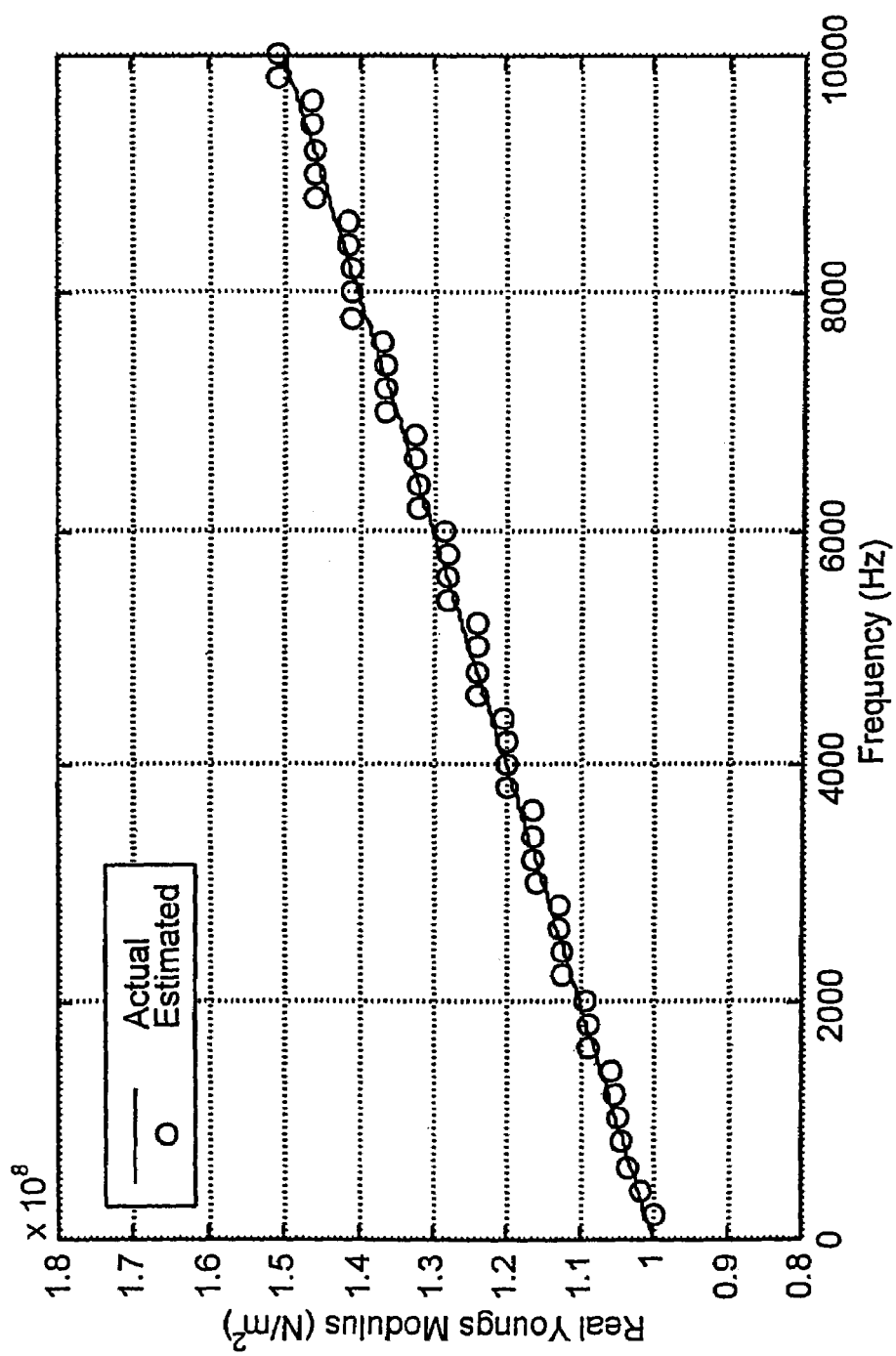
FIG. 13 is a plotted graph depicting the actual Young's modulus and the estimated Young's modulus versus the frequency with the real component.
Figure 14:
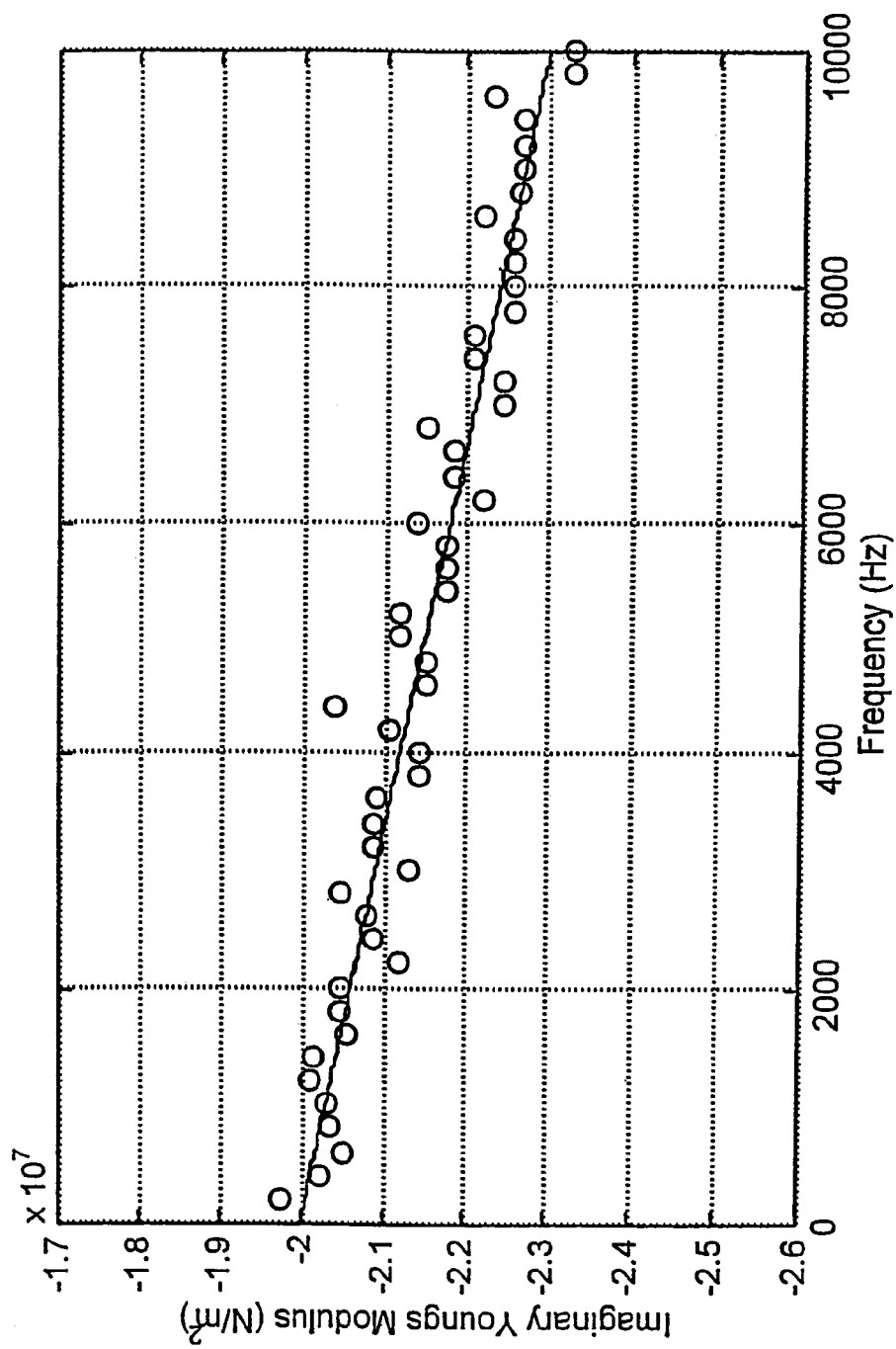
FIG. 14 is a plotted graph depicting the actual Young's modulus and the estimated Young's modulus versus the frequency with the imaginary component.
Figure 15:
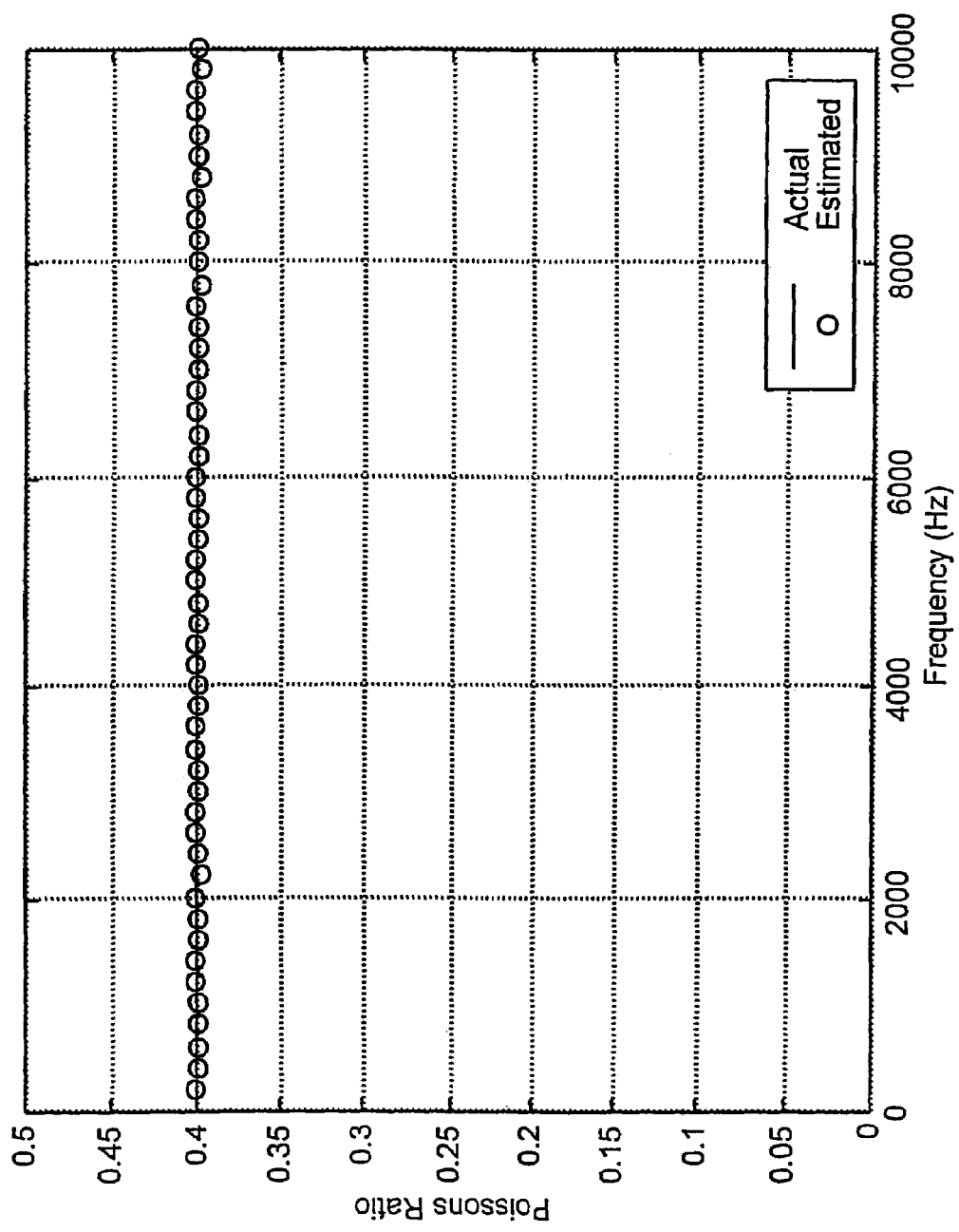
FIG. 15 is a plotted graph depicting the actual Poisson's ratio and the estimated Poisson's ratio versus the frequency.

FIGS. 13 and 14 are plots of the actual Young's modulus (solid line) and the estimated Young's modulus (o symbol) versus the frequency. FIG. 13 depicts the real component and FIG. 14 depicts the imaginary component. Finally, FIG. 15 is a plot of the actual Poisson's ratio (solid line) and the estimated Poisson's ratio (o symbol) versus frequency. Because the numerical example is formulated using a Poisson's ratio that is strictly real, no imaginary component is shown in this plot. Imaginary values of Poisson's ratio are possible and have been shown to theoretically exist (See T. Pritz, "Frequency Dependencies of Complex Moduli and Complex Poisson's Ration or Real Solid Materials," *Journal of Sound and Vibration*, Volume 214, Number 1, 1998, pp. 83–104).

The major advantages of this new method is the ability to estimate complex dilatational and shear wavespeeds of a material that is slab-shaped and subjected to insonification; the ability to estimate complex Lamé constants of the material; the ability to estimate complex Young's and shear moduli of the material and the ability to estimate complex Poisson's ratio of the material.

Thus by the present invention its objects and advantages are realized and although preferred embodiments have been disclosed and described in detail herein, its scope should be determined by that of the appended claims.

What is claimed is:

1. A frequency domain method to estimate a real and imaginary dilatational wavespeed of a material, said method comprising the steps of:

providing a specimen of the material;

providing a source of acoustic waves at a zero wavenumber;

positioning said specimen at a distance from said source such that said acoustic waves conform to plane waves;

exciting said specimen with said acoustic waves for at least two nonzero wavenumbers;

measuring frequency domain transfer function data subsequent said excitation of said specimen for at least two nonzero wavenumbers;

calculating said frequency domain transfer function data to closed form subsequent to said measuring step of said specimen for said excitation for at least two nonzero wavenumbers;

determining the real and imaginary dilatational wavespeed of said specimen from said calculated frequency domain transfer function data;

determining an estimated real and imaginary shear wavespeed of the material from said frequency domain transfer function data calculated to closed form subsequent to said measuring step of said specimen for said excitation for at least two nonzero wavenumbers; and obtaining a real and imaginary shear modulus using a grid method of the material from said real and imaginary determined shear wavespeed.

2. The method in accordance with claim 1, said method comprising the further step of determining a real and imaginary Young's modulus of the material from said obtained shear modulus.

3. The method in accordance with claim 2, said method comprising the further step of obtaining an estimated Poisson's ratio of the material form said determined Young's modulus and said obtained shear modulus.

* * * * *

UNITED STATES PATENT AND TRADEMARK OFFICE
CERTIFICATE OF CORRECTION

PATENT NO. : 7,062,386 B1  Page 1 of 1
APPLICATION NO. : 10/730194
DATED : June 13, 2006
INVENTOR(S) : Andrew J. Hull It is certified that error appears in the above-identified patent and that said Letters Patent is hereby corrected as shown below:

Change title of Patent from "METHOD TO ESTIMATE THE MECHANICAL PROPERTIES OF A SOLID MATERIAL SUBJECTED TO ISONIFICATION" to --METHOD TO ESTIMATE THE MECHANICAL PROPERTIES OF A SOLID MATERIAL SUBJECTED TO INSONIFICATION--.

Col. 3, line 41, change "isonification" to --insonification--.

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,062,386 B1
APPLICATION NO. : 10/730194
DATED : June 13, 2006
INVENTOR(S) : Andrew J. Hull It is certified that error appears in the above-identified patent and that said Letters Patent is hereby corrected as shown below:

Item [54] and Column 1, lines 1-4
Change title of Patent from "METHOD TO ESTIMATE THE MECHANICAL PROPERTIES OF A SOLID MATERIAL SUBJECTED TO ISONIFICATION" to --METHOD TO ESTIMATE THE MECHANICAL PROPERTIES OF A SOLID MATERIAL SUBJECTED TO INSONIFICATION--.

Col. 3, line 41, change "isonification" to --insonification--.

This certificate supersedes the Certificate of Correction issued December 30, 2008.

Signed and Sealed this

Third Day of February, 2009

JOHN DOLL
*Acting Director of the United States Patent and Trademark Office*